United States Patent
Larsen

(10) Patent No.: US 6,959,618 B1
(45) Date of Patent: Nov. 1, 2005

(54) PARTICLE CHARACTERIZATION APPARATUS

(75) Inventor: Ulrik Darling Larsen, Holte (DK)

(73) Assignee: Chempaq A/S, Copenhagen (DK)

(*) Notice: Subject to any disclaimer, the term of this patent is extended or adjusted under 35 U.S.C. 154(b) by 0 days.

(21) Appl. No.: 10/048,835

(22) PCT Filed: Aug. 3, 2000

(86) PCT No.: PCT/EP00/07537

§ 371 (c)(1),
(2), (4) Date: Feb. 6, 2002

(87) PCT Pub. No.: WO01/11338

PCT Pub. Date: Feb. 15, 2001

(30) Foreign Application Priority Data

Aug. 6, 1999 (DK) .................. 1999 01108

(51) Int. Cl.[7] .................. G01N 15/00; G01N 27/00
(52) U.S. Cl. .................. 73/865.5; 73/61.71; 324/71.1
(58) Field of Search .................. 73/865.5, 61.71, 73/61.73; 324/71.1

(56) References Cited

U.S. PATENT DOCUMENTS

| | | | |
|---|---|---|---|
| 2,656,508 A | * 10/1953 | Coulter | 324/71.1 |
| 3,395,343 A | * 7/1968 | Morgan et al. | 324/71.1 |
| 3,902,115 A | 8/1975 | Hogg et al. | |
| 3,958,177 A | * 5/1976 | Reeves et al. | 73/865.5 |
| 4,014,611 A | * 3/1977 | Simpson et al. | 324/71.4 |
| 4,600,880 A | * 7/1986 | Doutre et al. | 324/71.1 |
| 4,607,526 A | 8/1986 | Bachenheimer et al. | |
| 4,738,827 A | 4/1988 | Pierotti | |
| 4,760,328 A | 7/1988 | Groves | |
| 5,198,749 A | * 3/1993 | Guthrie et al. | 324/71.4 |
| 5,241,262 A | * 8/1993 | Guthrie et al. | 324/71.4 |
| 5,500,992 A | 3/1996 | Barnes et al. | |
| 5,716,852 A | 2/1998 | Yager et al. | |
| 5,804,022 A | 9/1998 | Kaltenbach et al. | |
| 5,911,871 A | 6/1999 | Preiss et al. | |
| 5,979,251 A | * 11/1999 | James et al. | 324/71.4 |

FOREIGN PATENT DOCUMENTS

| | | |
|---|---|---|
| EP | 0 844 475 A2 | 5/1998 |
| WO | WO 97/24600 | 7/1997 |
| WO | WO 98/50777 | 11/1998 |
| WO | WO 98/54568 | 12/1998 |
| WO | WO 99/01742 | 1/1999 |

OTHER PUBLICATIONS

"Fundamentals of Clinical Hematology", W.B. Stevens, Saunders Company, 1997.
"A Microfabricated Fluorescence–activated Cell Sorter", Anne Y. Fu et al., Nature Biotechnology, Vol 17, pp. 1109–1111, Nov. 1999.
"Electrical Resistance Pulse Sizing: Coulter Sizing", V. Kachel, Flow Cytometry and Sorting, Second Edition, Wiley–Liss, Inc., pp. 45–80, 1990, no month.
"Fundamentals of Microfabrication", M. Madou, CRC Press LLC, pp. 1–32, 1997, no month.
"Micromachined Electrical Field–Flow Fractionation ($\mu$–EFFF) System", B.K. Gale et al., IEEE, pp. 119–124. 1997.

* cited by examiner

Primary Examiner—Michael Cygan
(74) Attorney, Agent, or Firm—Volentine Francos & Whitt, PLLC

(57) ABSTRACT

An apparatus is provided for characterizing cells in a biological liquid sample and operating according to the Coulter principle. The apparatus has a disposable sensor unit and a docking station for removably receiving the sensor unit. The sensor unit housing contains electrodes in each of two chambers separated by a wall containing an orifice. The housing is adapted to contain and retain for disposal liquid pumped through the orifice during particle characterization operations.

17 Claims, 8 Drawing Sheets

6, 10 AND 9, 15 μm LATEX PARTICLES

BEADS: 9.146 μm

WHOLE BLOOD

RAW MILK SAMPLE

| Test no. | Coulter (>10 μm) | | Coulter (1% fat correct) | | Fossomatic | |
|---|---|---|---|---|---|---|
| | Count | mastitis | count | mastitis | count | mastitis |
| 1 | 761 | Yes | 364 | No | 99 | No |
| 2 | 3120 | Yes | 2780 | Yes | 8993 | Yes |
| 3 | 540 | Yes | 210 | No | 196 | No |
| 4 | 750 | Yes | 508 | Yes | 1890 | Yes |
| 5 | 4100 | Yes | 3700 | Yes | 7341 | Yes |

FIG. 8
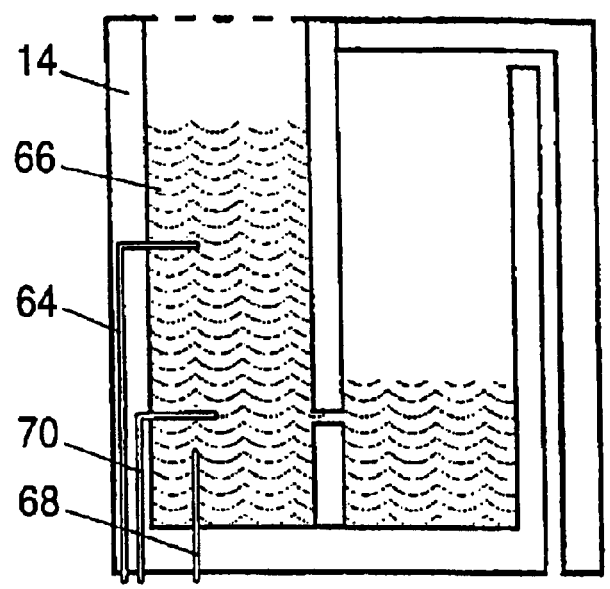
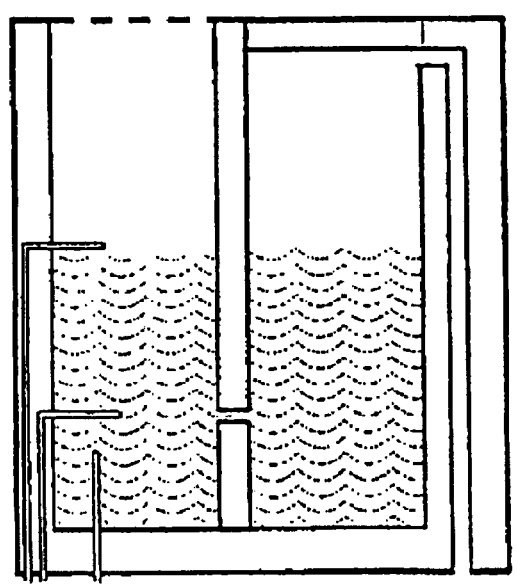
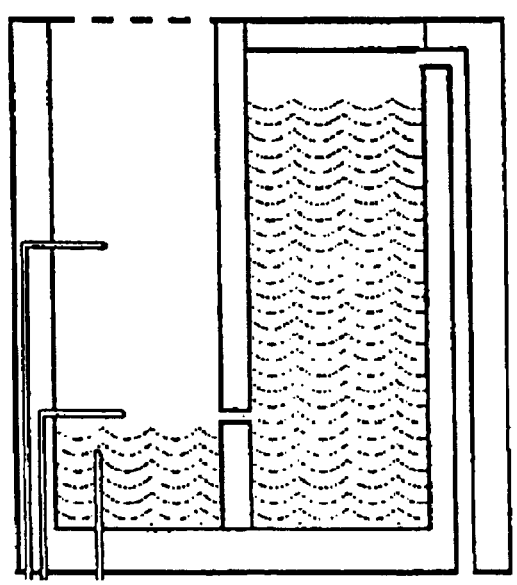

PARTICLE CHARACTERIZATION APPARATUS

This application is the national phase under 35 U.S.C. § 371 of PCT International Application No. PCT/EP00/07537 which has an International filing date of Aug. 3, 2000, which designated the United States of America and was published in English.

The present invention relates to particle characterisation apparatus in which particles suspended in a liquid are passed through an orifice, in principle in single file, to enable the characterisation of the particles, for instance by Coulter counting.

By aspiration of particles through a small orifice the particles can be characterised with respect to size, concentration and conductivity by the use of an electrical impedance technique, widely known as the Coulter sizing (see V. Kachel, "Electrical Resistance Pulse Sizing: Coulter Sizing", Flow Cytometry and Sorting, Second Edition, pp. 45–80, 1990 Wiley-Liss).

Different methods involving optical and electrical ways of sizing particles are frequently used for diagnostics and are employed in sophisticated instruments, such as Flow cytometers and Coulter sizing equipment. Until now there have been only a few instruments available for particle counting and sizing, which still needs fairly expensive equipment that requires trained personnel to perform the measurements. There have been several groups working on micro-machined optical flow cytometers (A. Y. Fu et al, "A micro-fabricated fluorescence-activated cell sorter", Nature Biotechnology, Vol. 17, November 1999, pp. 1109–1111), which could be used as cheap portable instruments. However, these instruments still require precision fluidic dispensing, a laser and a sensitive detection system. As an alternative, the much simpler Coulter method (explained in next section) can be employed. Such an instrument would be limited to counting and sizing of cells but still be an attractive tool for a wide variety of applications, e.g. milk quality control and blood cell counting.

Counting and sizing of particles by the Coulter principle is an internationally respected method that is being used in most haematology-analysers and particle counting equipment (see FIG. 3). The method is based on measurable changes in the electrical impedance produced by non-conductive particles in an electrolyte. A small opening called the "aperture or orifice", connects two electrically isolated chambers, where electrodes has been provided to contact the electrolyte. The orifice applies an restriction to the electrical path, whereby a sensing zone is established through which the particles are aspirated. In the sensing zone each particle will give rise to a displacement of the surrounding electrolyte, thus blocking part of the current-path and giving rise to a voltage pulse. By this method several thousand particles per second can be characterised with high precision. As opposed to optical methods, this method is not depending on the particle morphology, colour or density.

Conventional instruments utilising the impedance technique are based on a fixed membrane with a precision-machined orifice, which is being maintained by flushing and rinsing the membrane. These procedures require cleaning— and flushing liquids, pumps and control electronics, which complicates and increase the cost of the instrument. In conventional Coulter counters, the orifices are formed in materials such as ruby or sapphire which are chosen for their dimensional stability under the conditions required for their fusion to glass in the construction of sensor elements. These commercially available particle analysers cannot be considered portable, which implies that all equipment are placed centrally in large laboratories. Furthermore, maintenance is obviously required.

Since many laboratories can not use the inflexible standard instruments or can not afford the cost of these, manual methods are still widely used for doing simple counting. These methods are based on a small microscope slide with well defined square markings known as a haemocytometer (see Stevens, "Fundamentals of Clinical Haematology", W.B. Saunders Company, 1997, ISBN 0-7216-4177-6); The sample is injected in between the gap from the haemocytometer and a cover glass placed on top of the markings. The haemocytometer is placed under a microscope and particles are counted manually. Manual counts are performed until a number of between 100–300 cells has been reached—a method carrying an error of approximately 10%. By electronic counting more than 10,000 cells can be counted within 1 minute, giving an error of 1% or better. Furthermore, timing is critical when counting with haemocytometers, since particles need a little time to settle, but waiting too long will cause an uneven distribution of cells due to evaporation from the open edges. It is not really possible to perform a measurement of cell size with a standard haemocytometer, but with an addition of a high resolution CCD-camera, cross-sectional cell size can be determined (see patent application WO 98/50777).

The cross-sectional area found by 2D images does not necessary relate to the volume of the particles, but depends on the axial symmetry. With the electrical impedance technique it is possible to resolve the particle volume from the measurement. By maintaining a constant current across the orifice, the recorded voltage pulse from particles displacing the electrolyte in the orifice will have a height proportional to the volume of the particle. This is because particles can be considered non-conducting compared to the electrolyte, the electrical field in the centre of the orifice is homogeneous, which is normally the case when the diameter is smaller than the length of the orifice (l/D>1), the particle is to be considered small compared to the diameter of the orifice (d<0.2*D), only one particle passes through at a time and the particles are passed through the orifice in the axial path.

In a first aspect, the present invention provides apparatus for characterising particles suspended in a liquid, said apparatus comprising:

a sensor unit which comprises
  a housing comprising a collection chamber bounded by a wall containing an orifice for the passage of said particles,
  said collection chamber having an inlet/outlet for connection to a source of positive or negative gas pressure,
  wherein said sensor unit further comprises components of a particle characterisation device for characterising particles passing through said orifice in use, which components are functionally addressable from outside said housing,
a docking station for receiving said sensor unit,
a source of positive or negative gas pressure operatively connected to a port in said docking station, said port being such that when said sensor unit is received in said docking station said port forms a gas connection with said collection chamber inlet/outlet,
means in said docking station for functionally addressing said components of a particle characterisation device of said sensor unit,
and further components of said particle characterisation device located remotely from said sensor unit and operatively connected to said component addressing means of the docking station.

Normally such apparatus is operated so that the flow through said orifice is into the collection chamber.

In some preferred embodiments, the housing is divided into a first chamber and said collection chamber by said wall containing the orifice. The first chamber may then have a breather inlet/outlet for communication with the atmosphere.

Preferably, the sensor unit is designed to be disposable after a single use. It is desirable that after use there is no need to clean the remainder of the apparatus before it can be used in a new assay procedure with a new sensor unit. Accordingly, one should avoid the escape of liquid from the sensor unit and its entry into the docking station. To this end the positioning of the orifice with respect to the breather inlet/outlet, the second chamber inlet/outlet and said particle characterisation device components is preferably such that a volume of liquid sufficient for the desired particle characterisation can be drawn or pumped through the orifice without the liquid passing out of the housing. Generally, it should be possible to pass a volume of liquid which is at least 1 ml, e.g. 5 ml, through the orifice whilst particle characterisation measurements are being made without the liquid overflowing out of the housing.

Preferably, said components of the particle characterisation device associated with the sensor unit include a first electrode in said first chamber and a second electrode in said second chamber, each said electrode being electrically connected to a terminal member accessible from the exterior of said sensor unit, and said means in said docking station for functionally addressing said components comprises respective electrical connector members for connecting to said terminal members. Generally, it is preferred that all necessary electrical and fluid connections to the sensor unit can be established by fitting the sensor unit into the docking station, preferably by a simple push fit.

In one preferred arrangement, the inlet/outlet of the second chamber of the sensor unit leads from a head space in said second chamber through a conduit formed in said housing to a port positioned at the bottom of said housing which co-operates with said port of the docking station. The sensor unit may then be a push fit downwards into the docking station.

Alternatively, the inlet/outlet of the second chamber of the sensor unit leads from a head space in said second chamber through a conduit formed in said housing to a port positioned at the top of said housing which co-operates with said port of the docking station. The sensor unit may then be a push fit upwards into the docking station.

Preferably, said orifice is formed by a process of photolithography, e.g. in a silicon wafer. By fabricating the orifice wafers (also known as 'count wafers') for a Coulter counter in such a way, these become much cheaper than orifice wafers for conventional counters on the market. The allows the manufacturing of a sensor unit cheaply integrating the necessary chamber, aperture and electrodes. By doing this, the sensor unit can be used as a disposable unit, which removes the need for the washing and rinsing of the aperture as in conventional instruments. Furthermore it is not necessary to use time to switch the instrument for the size of particles in subject, since this will be specific to the used aperture. The disposable chamber may contain a standard solution (a liquid with known concentration of particles) that can be used for calibrating the sizes and for determination of concentrations. The chambers can be constructed such that the liquids will remain inside the chamber, such that the instrument in which it will be placed will not require rinsing after use.

Preferably, said apparatus includes means for determining the beginning and end of a period during which a predetermined volume of liquid has passed through said orifice.

This may include the provision of a secondary electrode in the first or the second chamber positioned for sensing when liquid in said chamber is at or above a first level, which secondary electrode is connected to a terminal member accessible from the exterior of said sensor unit, and said docking station may then comprise an electrical connector member for connecting to said terminal member of the secondary electrode.

There may be a further secondary electrode in the same chamber as said secondary electrode and positioned for sensing when liquid in said chamber is at or above a second level, which further secondary electrode is connected to a terminal member accessible from the exterior of said sensor unit, and said docking station may comprise an electrical connector member for connecting to said terminal member of the further secondary electrode.

These secondary electrodes may be used for sensing when the level of the liquid is such that the respective secondary electrodes are or are not immersed in the liquid and may therefore serve for determining the beginning and end of a period during which a fixed volume of liquid has passed through the orifice. For instance, particle characterisation may begin when the level of the liquid just falls below the level of a first said secondary electrode and may end when the level of the liquid just falls to below a second of the secondary electrodes, the volume of liquid passing out of the chamber containing the secondary electrodes during this period being defined by the separation of the secondary electrodes. Of course, it is not necessary that the secondary electrodes be in the chamber from which liquid passes through the orifice, they could equally well be in the chamber into which the liquid flows and both secondary electrodes do not need to be in the same chamber.

Where the end point of the passage of a defined volume of liquid is the effective emptying of one chamber to below the level of the orifice, it is preferred that each of the first and second chambers (or at least that chamber from which liquid passes) has a transverse cross sectional area at the level of said orifice which is substantially less than the transverse cross sectional area of said chamber over a substantial part of the height of the chamber above said orifice.

The invention includes a sensor unit for apparatus for characterising particles suspended in a liquid which sensor unit comprises:

a housing divided into a first chamber and a second chamber separated by a wall containing an orifice for the passage of said particles, said first chamber having a breather inlet/outlet for communication between a head space in said first chamber and the atmosphere and said second chamber having an inlet/outlet for connection to a source of positive or negative gas pressure which leads from a head space in said second chamber through a conduit formed in said housing to a port positioned at the bottom of said housing.

Said sensor unit may comprise components of a particle characterisation device for characterising particles passing through said orifice in use, which components are functionally addressable from outside said housing, e.g. a respective electrode in each chamber. Preferably therefore, said components of the particle characterisation device associated with the sensor unit include a first electrode in said first chamber and a second electrode in said second chamber, each said electrode being electrically connected to a terminal member accessible from the exterior of said sensor unit.

Preferably, said orifice is formed by a process comprising photo-lighography, e.g. in a silicon wafer.

Preferably, the sensor unit comprises a secondary electrode in the first or the second chamber positioned for sensing when liquid in said chamber is at or above a first level, which secondary electrode is connected to a terminal member accessible from the exterior of said sensor unit and preferably the sensor unit comprises:

a further secondary electrode in the same chamber as said secondary electrode and positioned for sensing when liquid in said chamber is at or above a second level, which further secondary electrode is connected to a terminal member accessible from the exterior of said sensor unit.

Optionally, each of the first and second chambers has a transverse cross sectional area at the level of said orifice which is substantially less than the transverse cross sectional area of said chamber over a substantial part of the height of the chamber above said orifice.

In a second independent aspect, the invention provides particle characterising apparatus in which particles are characterised as they are passed through an orifice, wherein said orifice is formed by a process comprising photo-lithography, e.g. in a silicon wafer.

An orifice may suitably be formed in a photo-reactive polymer by photo-lithography and subsequent development. Thus a free standing sheet of polymer of the kind used conventionally as a photoresist material may be exposed to light to solubilise a spot to be removed to define an orifice (or to insolubilise the non-spot forming areas) followed by development with solvent to remove material to form the orifice. Normally, a large number of count wafers each containing a respective orifice will be made simultaneously in one sheet. Suitable photoresist polymers are described in e.g. M. Madou "Fundamentals of Microfabrication; CRC Press LLC, 1997, ISBN 0-8493-9451-1. They include AZ-5214E, SU8, polyimides and others.

Alternatively, the photoresist polymer may be used as a protecting layer over a substrate such as silicon or any other etchable material in which the orifice is formed by etching regions exposed by development of the photoresist. If the etched substrate is electrically conducting it may be insulated prior to use by the formation of a suitable insulating layer thereover. The photoresist polymer may be used as such a layer.

Count wafers made lithographically may be used in all forms of apparatus and method according to this invention.

In a third aspect, the invention provides a method of operating particle characterisation apparatus comprising a demountable sensor unit containing a count orifice serving as an inlet to a chamber initially containing a volume of air and having a connection to an air pump whereby air may be pumped to induce flow of sample liquid through said orifice into said chamber, said method comprising passing liquid containing particles through said orifice into said chamber and making particle characterising measurements for a period such that said liquid does not fill said chamber, disconnecting said sensor unit from said apparatus with all of the liquid that has passed into said chamber and discarding said sensor unit.

For use in such a method, the invention includes apparatus for characterising particles suspended in a liquid, said apparatus comprising:

a sensor unit which comprises a tubular housing defining a chamber which has a wall containing an orifice for the passage of said particles and which extends upwardly from the level of said orifice, a docking station for receiving said sensor unit, a source of positive or negative gas pressure operatively connected to a port in said docking station, said port being located such that when said sensor unit is received in said docking station said port forms a gas connection with said chamber above said orifice, a first electrode extending inside said chamber when said sensor unit is in place in said docking station, and a second electrode disposed outside of said chamber when said sensor unit is in place in said docking station, wherein, said chamber has a volume of at least 1 ml.

Generally, in all embodiments it is preferred that all components which are wet by the sample in use are disposable and all non-disposable components can be re-used without cleaning.

The invention will be further described and illustrated with reference to the accompanying drawings in which:

FIG. 8 is a side cross sectional view of a sensor unit for use in a third preferred embodiment of the invention, shown in three stages (A, B and C) of use;

Figure 1:
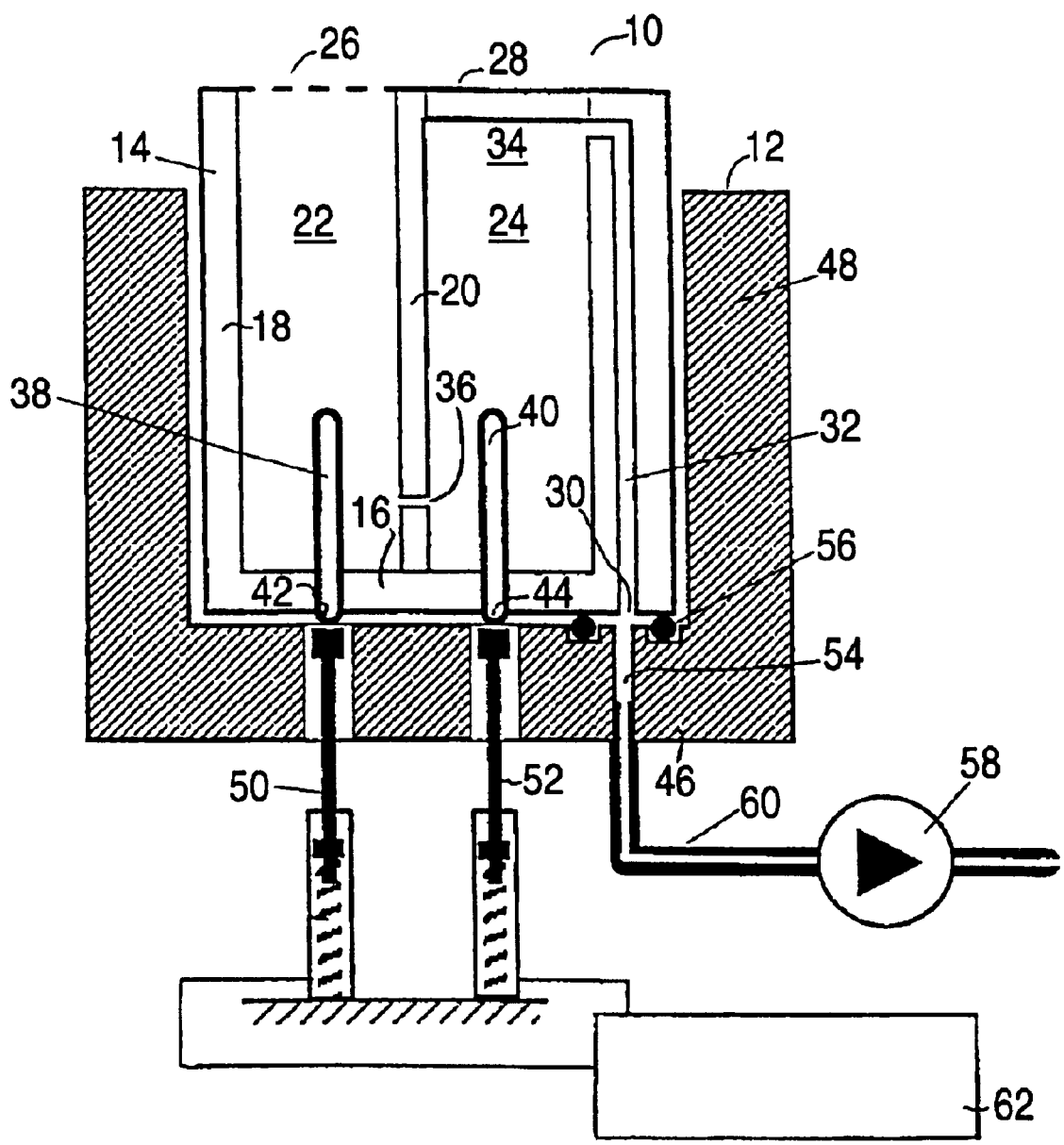
FIG. 1 is a cross sectional side view through a sensor unit and docking station of apparatus according to a first preferred embodiment of the invention.

The apparatus shown in FIG. 1 comprises a sensor unit 10 and a docking station 12.

The sensor unit comprises a housing 14 having a base wall 16 and a circumambient side wall 18 with a wall 20 rising from the base and separating the housing into two chambers; a first or 'open' chamber 22 and a second or 'closed' chamber 24. At the upper end of first chamber 22 there is provided a removable membrane seal 26, providing a temporary closure which is removed for use. At the top of the second chamber there is a top wall 28 which closes the chamber. An orifice in the bottom wall of the housing forms an outlet/inlet 30 from which ascends a conduit 32 formed in the wall of the chamber. Conduit 32 ends short of the top wall 28 and so communicates with a head space 34 within said chamber 24.

The dividing wall 20 has a count wafer (not shown) received over a through hole therein and defining a count orifice 36 positioned somewhat above but quite close to the base wall 16. Each chamber has an electrode 38,40 extending from an external terminal 42,44 through the base wall 16 and up to a level within its respective chamber which is somewhat above the level of the count orifice 36.

Particles can be aspirated through the orifice by pressure driven flow in either direction. When a saline or other electrolytic liquid solution is added to the chambers, the two chambers will be electrically isolated from each other except for the route for current flow provided by the passage through the orifice.

The docking station 12 has a cup shaped housing having a base 46 and a circumambient side wall 48. In the base 46 there are respective spring loaded electrical connectors 50,52 for contacting the terminals 42,44 of the sensor unit automatically when the sensor unit is received as a push fit into the docking station. There is also a conduit 54 passing through the base wall 46 aligned with the conduit 32 of the sensor unit. Conduit 54 at its opening into the upper face of the wall 46 has an O-ring seal for forming a gas tight connection with the lower face of the base wall 16 of the sensor unit.

A vacuum pump 58 is connected by a line 60 to the lower end of the conduit 54. In a modification of the apparatus, the vacuum pump 58 can be reversed so as to apply positive gas pressure to the conduit 54.

Schematically indicated at 62 are the further conventional components of a Coulter counter including all the electronic circuitry and display equipment needed for the operation of the apparatus.

The docking station is embodied in a portable instrument into which the sensor unit is a disposable plug-in component. The sensor unit is easily interconnected with the docking station by placing it in the docking station receptacle as illustrated in FIG. 1. The sensor unit is placed in the docking station and fixed with a easy pressure downwards. The electrical contacts to the electrodes are established automatically upon insertion and hermetic sealing to the opening of the suction conduit 32 is automatically established so that suction can be applied by the small air pump 58.

The sensor unit housing can be partly fabricated with cheap mass-production techniques such as polymer injection moulding. Electrodes can be made of small rods of metal or graphite. The orifice can be made very precisely with Silicon photolithography and various etching techniques (wet etching and dry etching, see e.g. "Fundamentals of microfabrication", Marc Madou, CRC Press LLC, ISBN 0-8493-9451-1) and placed in the separating wall. The surface of the silicon wafer containing the orifice may be made electrically insulating by forming a layer of silicon dioxide or silicon nitride over the wafer by baking in an oven in a suitable atmosphere.

Sample liquid with particles in suspension can be applied to the open chamber of the sensor unit. Applying a negative pressure difference to the closed chamber through the conduit 32, will cause the liquid to be sucked through the orifice and into the closed chamber. The suction outlet is led from the head space near the top of the closed chamber, so that only air is sucked out as long as the liquid is below this level. This implies that the docking station is and the remainder of the instrument does not have to be cleaned as would be the case after contact with biological material.

The chambers can be pre-filled with liquids (preferably an electrolyte) and calibration particles for the measurement. This implies that the sensor unit is ready for use before the insertion into the docking station. These particles can be used for calibration of the sizing or as a measure of particle concentration in the sample, if these can be differentiated from the calibration particles. If the concentration of calibration particles is known it is not necessary to know either volume or concentration of the particles in the sample to determine this. The concentration is given by $C1=n1/n2*C2$, where $C1$ is the concentration to be found, $C2$ is the known concentration of calibration particles, $n1$ is the number of counted particles from the sample and $n2$ is the number of counted particles from the calibration standard.

Figures 6, 7:
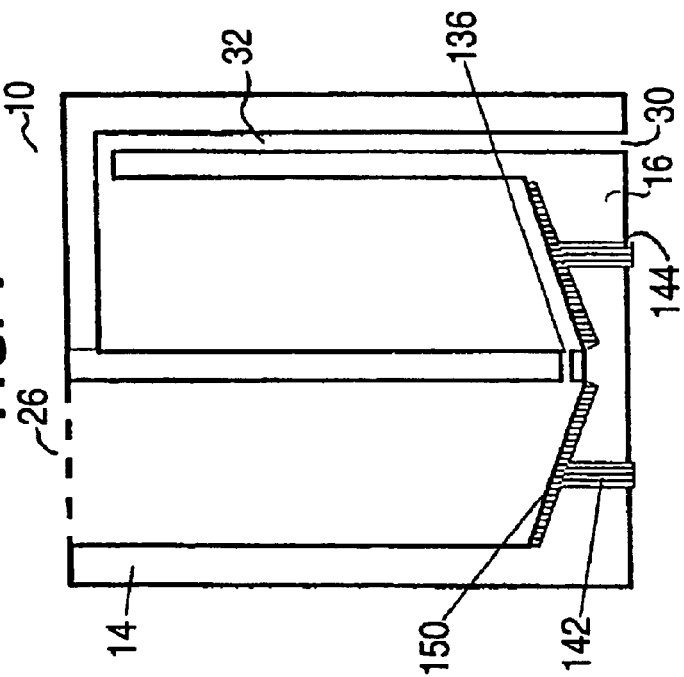
FIG. 6 is a table of results obtained in Example 4.
FIG. 7 is a side cross sectional view of a sensor unit for use in a second preferred embodiment of the invention.

If no calibration particles are present, the concentration of particles in the sample can be determined by control of the volume sucked through the orifice. The apparatus can be configured so that one can determine when a known volume of liquid has been passed through the orifice. This can be done by constructing the container in a way, that would allow the liquid to be removed essentially totally from the open chamber to the closed chamber or at least such that the volume removed by lowering the level in the open chamber to the level of the count orifice is reasonably precise. A way to do this is illustrated in FIG. 7. By sloping the upper surface of the bottom wall 16 of the housing and placing the orifice 136 and electrodes 142, 144 near the bottom of the well so formed in each chamber, it will be possible to suck almost all liquid through the orifice, while contact to the electrodes still remains through electrical connector 150. The volume passed is then determined by the starting volume in the open chamber. The advantage of this method is that the desired applied sample volume may differ in different tests.

As an alternative means of determining the volume passed, one may place secondary electrodes in the chambers that indicate the level of the electrolyte by sensing the presence of conductive media as depicted in FIG. 8. The electrodes 38,40 will be present as in FIG. 1, but are not shown. A high level secondary electrode 64 placed in the open chamber of the housing indicates when the electrolyte 66 is above this level by measurement of the conductivity towards a reference electrode 68. A low level secondary electrode 70 indicates when the level of the electrolyte is above this level by measurement of conductivity towards the reference electrode. The beginning and the end of the passage of the controlled volume is indicated by zero conductivity between reference electrode and respective level electrodes. The volume will be the volume between the two level electrodes. In situation (A) the liquid covers both level electrodes. In situation (B) the liquid is just below the high level electrode, thus leading to no conductivity between this and the reference. In situation (C) the liquid is just below the low level electrode, thus leading to no conductivity between this and the reference. It is not necessary to control the volume filled into the chamber, as long as the top level electrode is well covered by sample before the run. Since the common electrode for the impedance measurement is used as current source, this should normally be used as reference electrode too. Other configurations of the electrodes could be applied in order to make a level reference.

Figure 9:
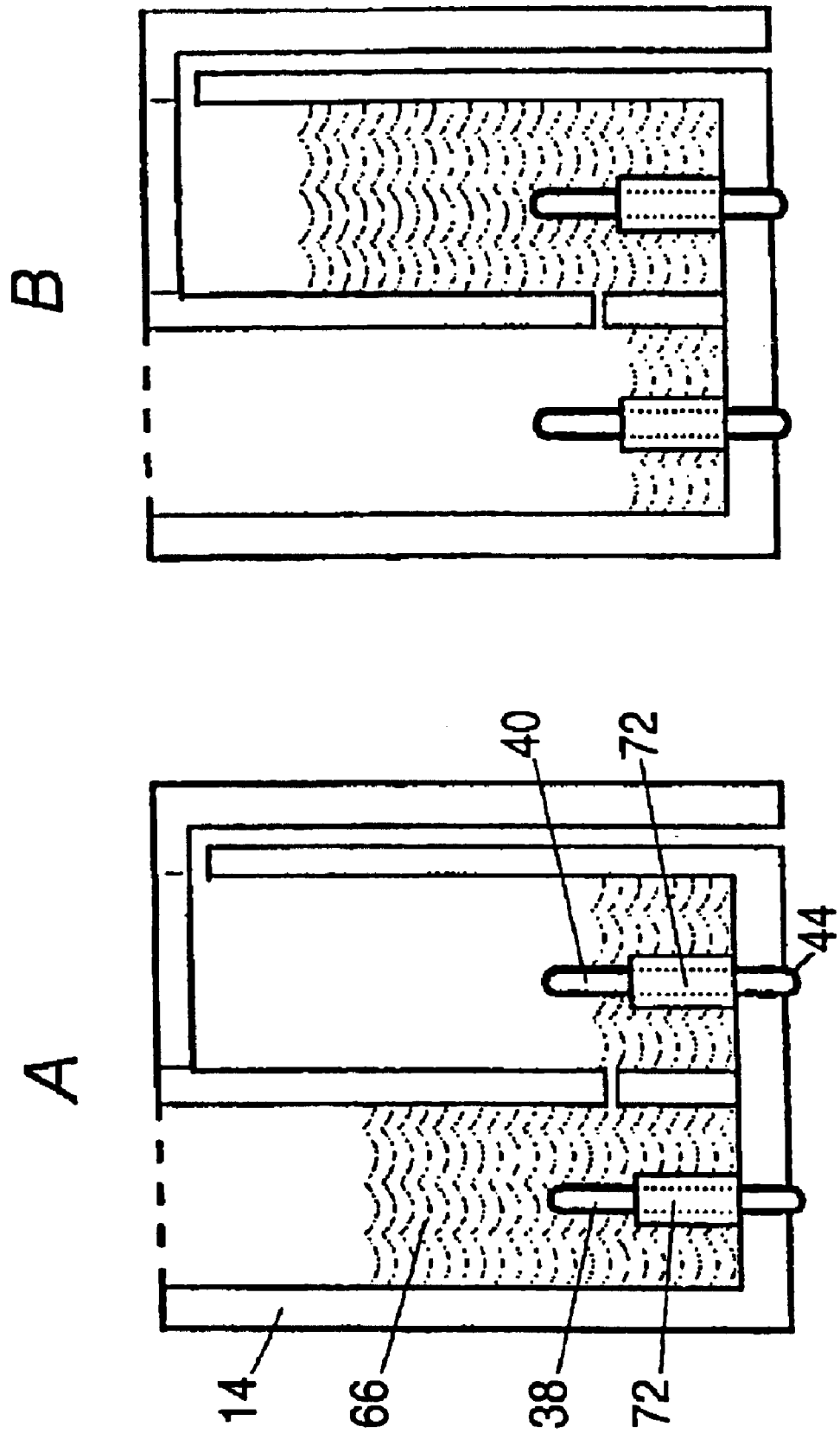
FIG. 9 is a side cross sectional view of a sensor unit for use in a fourth preferred embodiment of the invention, shown in two stages (A and B) of use.

Finally, since the electrodes 38,40 placed in the chambers are needed in order to count particles, the contact to these will in fact indicate the presence of conductive media. This could be used to indicate the levels of the electrolyte in the two chambers as illustrated in FIG. 9. The electrodes 38,40 are conductive from a certain level and up, which can be established by making the lower part of the electrode non-conductive, e.g. by a non-conductive sleeve 72. When a measured volume of the electrolyte 66 is added to the open chamber 22 of the housing 14 there is no contact between the electrodes. In this situation no pulses will be counted. After a short while, as suction is applied, the level in the closed chamber will reach the conducting portion of the electrode 40 (situation (A)). The counting will start automatically and end when the level in the open chamber is below the level of the non-conductive sleeve of the electrode 38 (situation (B)). This method allows different amounts of sample to be used, and the counting will be of particles in the volume applied less the volume below the conductive part of the electrode 40. This method is somewhat similar to the first method described with reference to FIG. 7 in which the chambers each had a sloped bottom, but in this case the chambers are not empty when the counting starts and ends, which may be of importance, when the electronic path should be established before the measurement. If the electronic path has not been established, the signals from the impedance measurement may be quite noisy in the beginning and the end, which will then have to be disregarded in the counting by electronics.

Figure 10:
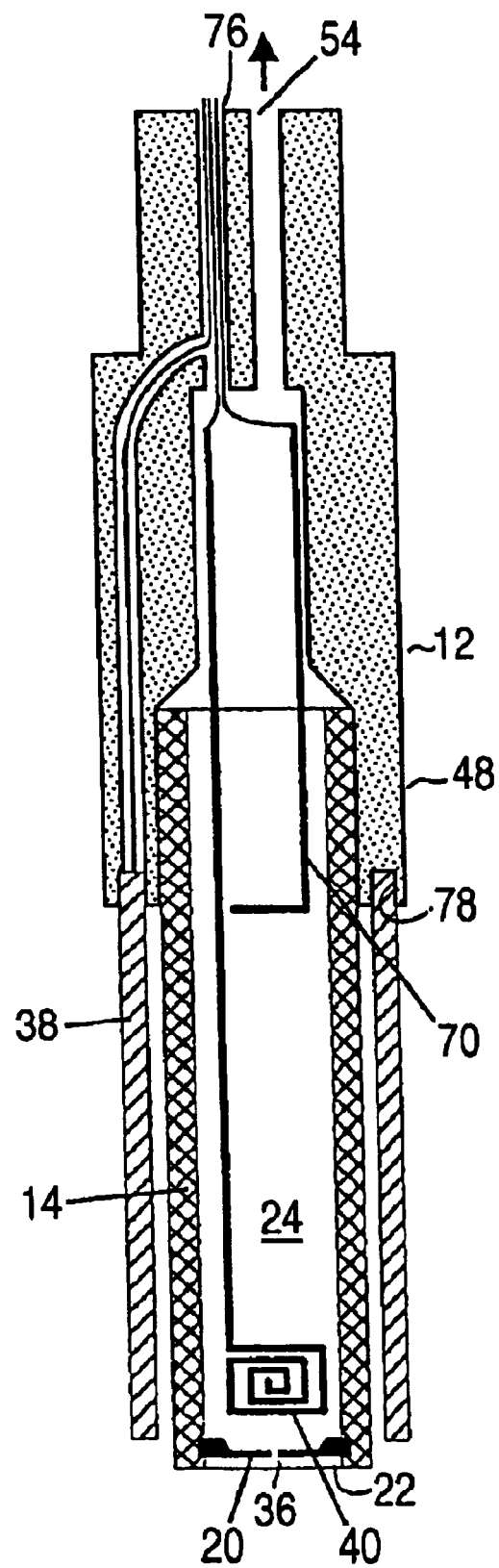
FIG. 10 is a longitudinal cross-section of a sensor unit and docking station of a fifth preferred embodiment of apparatus of the invention.

An alternative form of disposable sensor unit and its associated docking station is shown in FIG. 10. It illustrates at least the second and third aspects of the invention. Here the first or open chamber 22 is vestigial and could be omitted entirely. The sensor unit has a housing in the form of a cylindrical tube 14 divided into an upper second chamber 24 and a lower said first chamber 22 by a partition wall 20 containing a count wafer defining a count orifice 36. The count orifice is formed in a silicon wafer attached in the centre of the wall 20. The partition wall 20 can be positioned as low in the tube 14 as desired, even at its extreme lower end.

Figure 11:
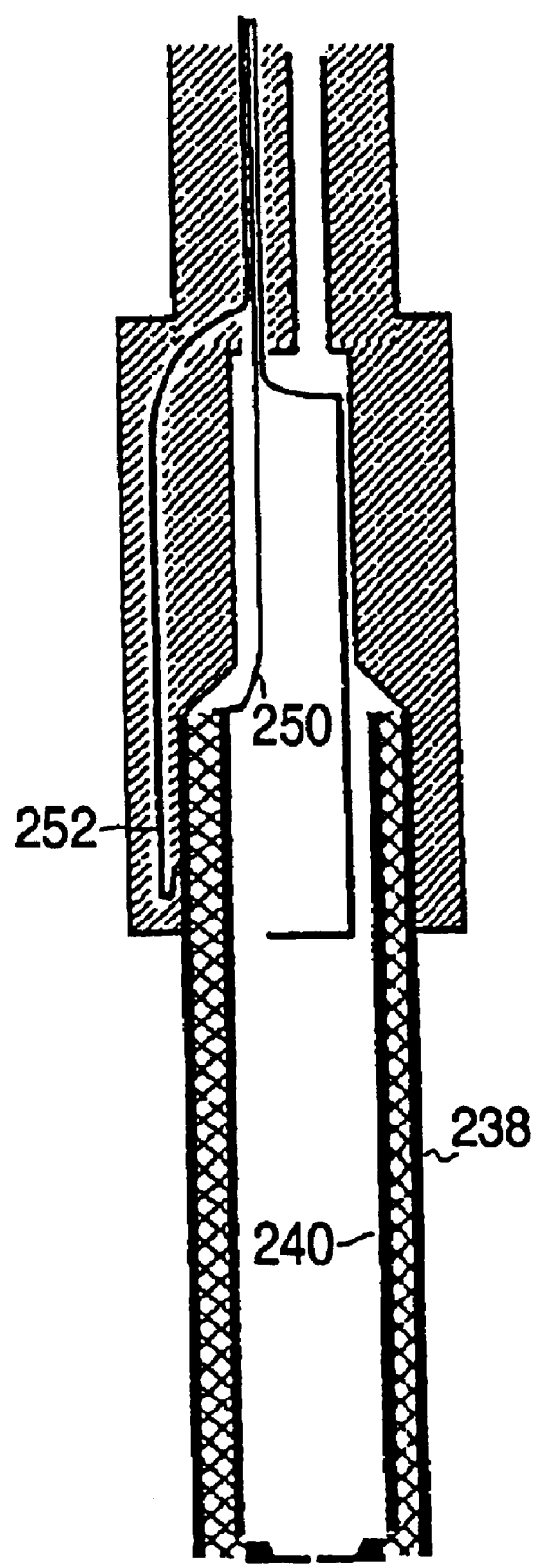
FIG. 11 is a longitudinal cross-section of a sensor unit and docking station of a sixth preferred embodiment of apparatus of the invention.

There are no electrodes forming part of the sensor unit in this embodiment but it could readily be modified such that the electrodes are attached to the tube 14. For instance, one electrode could be located as a tube on the inside of tube 14 with the other being located as a tube on the outside of tube 14 so that tube 14 acts as an insulating spacer between the two electrodes 240 and 238 as shown in FIG. 11. Also shown in FIG. 11 are electrical connectors 250 and 252. As shown, both of the sensing electrodes are associated with the docking station. The docking station 12 comprises a tubular body having a side wall 48 defining a socket at its lower end into which the sensor unit is an interference push fit. At its upper end the body of the docking station 12 encloses two conduits, one (54) being for the application of suction and being connected to a suction pump (not shown) and the other (76), being for the passage of electrical connecting wires to a first and a second measuring electrode and to a third, stop electrode. The first electrode 38 is tubular and is concentric with and outside of the tube 14. It is held in a downwardly facing circular slot 78 in the end of the wall 48. The second electrode 40 is a coiled wire electrode which extends within the tube 14 to just above the count orifice 36. The third or stop electrode 70 is positioned above electrode 40 and serves to indicate when liquid has been sucked into the space within the tube 14 to a desired maximum level. This embodiment may be used by dipping the tube 14 into an open reservoir of sample and drawing sample up through the count orifice by suction. The sensor unit is easily disconnected and replaced.

Alternatively, both the sensor unit 10 and the docking station 12 can form part of a disposable assembly, in which case the sensor unit can be permanently fixed in the docking station. The connecting wires of the electrodes can be terminated at connectors such that the whole assembly illustrated in FIG. 10 can be received in a separate further docking station (not shown) with connection automatically being made to the electrode terminal connectors and the vacuum line 54 upon insertion into the further docking station.

The methods described can be combined to give the best solution for the final application. The disposable sensor is particularly usable where portable, cheap, simple or flexible equipment is needed, such as in small laboratories, in measurements in the field or as a "point of care" diagnostic tool.

A suitable electrolyte for use in apparatus according to the invention is 0.1 m KCl in filtered water. When sample is applied to the electrolyte, the electrolyte to sample volumes should preferably be higher than 10. Sample preparation should preferably result in between $10^3$ to $10^5$ particles per ml. A vortexing of the sample before and after adding electrolyte is recommended. Particle diameters should be within 10 to 30 percent of the orifice diameter. Volume flow should normally be from 100 $\mu$L to 1 ml per minute.

For the measurement a constant electrical current of approximately 1 mA should preferably be applied. The source of electrical current should preferably have a signal to noise ratio (S/N) better than 50000. The response from the electrode should be filtered electronically by a band-pass filter. A second order Chebyscheff filter with centre frequencies around 1 kHz is suggested.

The use of the apparatus described above is further illustrated by the following examples.

EXAMPLE 1

Sizing of Polymer Beads

Figure 2:
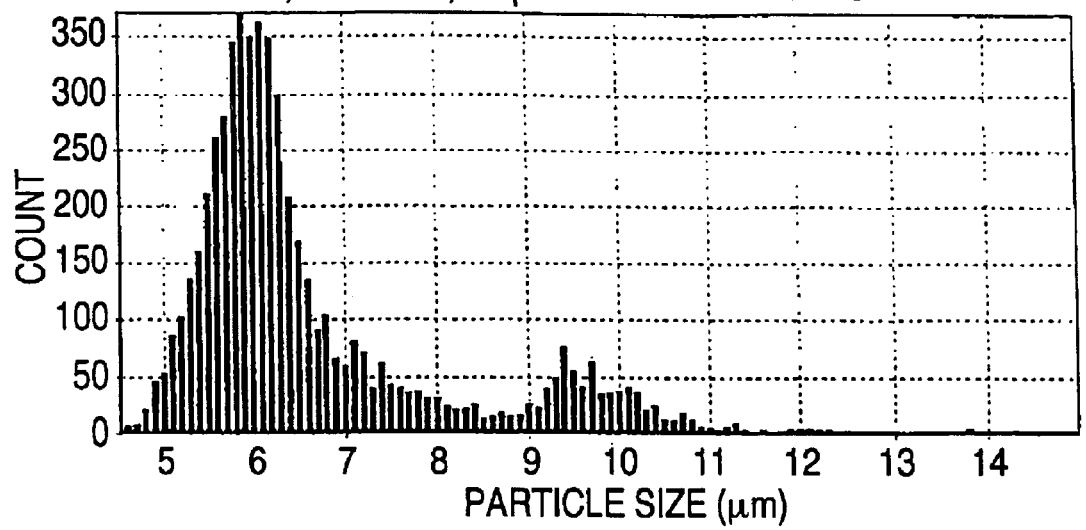
FIG. 2 is a graph showing results obtained in Example 1.

A mixture of 6.10 $\mu$m and 9.15 $\mu$m particles suspended in electrolyte was aspirated through the orifice of the apparatus shown in FIG. 1. The numbers of particles detected and the size of each detected particle were recorded. A bimodal distribution of detected particle size is clearly seen in FIG. 2.

The volumes of the particles are assumed to be proportional to the pulse height, which is only true within a certain interval. Because non-linearity is reproducible, particles that are out of range may be sized by using standard beads with known volumes. As can be seen from FIG. 2 the size of the 9.1 $\mu$m particle is determined to be approximately 0.8 $\mu$m larger than the specification. This may be explained by non-linearity of the scale and the existence of doublets and triplets.

EXAMPLE 2

Concentration Determination

Figure 3:
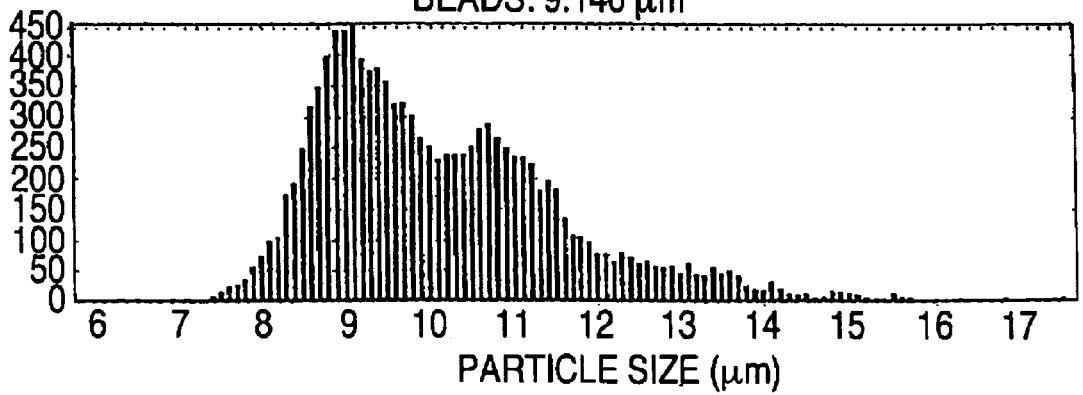
FIG. 3 is a graph showing results obtained in Example 2.

One of the most important, but also rather critical measurements to make with the counter is a concentration determination. In order to get an accurate concentration determination the particle suspension has to be homogeneous, the numbers of counted particles must be high enough and the amount of liquid going through the aperture must be controlled. Furthermore in association with the collection of data on the computer one must consider e.g. sample rate and trigger level. One of the more intrinsic problems is the occurrence of clusters of particles, whereof the most evident are doublets and triplets. These are most frequent when working with non-biological particles such as latex beads. In FIG. 3 the size distribution obtained with the silicon aperture is shown. The latex beads are 9.146 $\mu$m with a standard deviation of 0.577 $\mu$m. The doublets are double the volume, thus resulting in a mean diameter of 11.5 $\mu$m and in the same way triplets results in a mean diameter of 13.2 $\mu$m. Since the Gaussian distribution of single particles, doublets and triplets overlap, the exact number of these can not be found directly, and some mathematical calculations must be done. In this case approximately 20% of the counts were doublets and approximately 10% were triplets. This gives a multiplication factor to the number of single particles of 1.4. In biological samples doublets and triplets are not that common and will generally not cause problems.

The test was run three times with a total volume of the sample of 0.05 ml for each run giving a mean count of 11.384 particles with a standard deviation of 389 (3.4%). Using the correction factor of 1.4 this gives a total corrected concentration of: $319 \cdot 10^3 \pm 11 \cdot 10^3$ particles/ml. A small amount of sample was taken from the counting chamber and manually counted in a haemocytometer under a microscope. Two independent manual counting controls resulted in a concentration of: $314 \cdot 10^3 \pm 25 \cdot 10^3$ particles/ml. These experiments clearly establish that a good correlation exists between our Coulter counter results and the results from manual counting.

EXAMPLE 3

Blood Cell Counting

Figure 4:
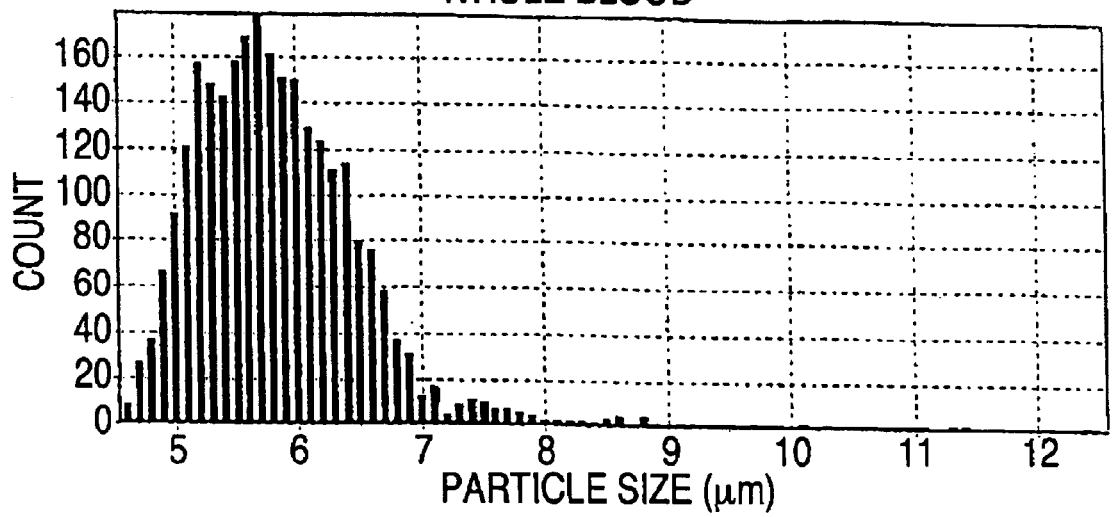
FIG. 4 is a graph showing results obtained in Example 3.

Measurement of blood cells has been performed and the result is shown in FIG. 4. Red blood cells are normally around 5 to 7 µm in diameter and are the most frequent in whole blood, as can be seen on the figure. Less frequent are white blood cells that are 6–10 µm in diameter. The distribution is a Gaussian curve, as it should be expected. Blood counts can be used in clinical diagnostics. It is fairly simple to count erythrocytes, leukocytes and thrombocytes by impedance measurements, which is considered the basic parameters for hematology (see "Fundamentals of Clinical Hematology", Stevens, W.B. Saunders Company, ISBN 0-7216-4177-6).

EXAMPLE 4

Counting Somatic Cells

Milk quality is essential for farmers, diary producers and consumers. Farmer have to deliver milk of a certain quality which is controlled by the so-called Somatic Cell Count (SCC). In milk quality tests somatic cells in the milk are counted to determine infections (clinical mastitis). A limit of 400,000 cells pr. ml. has to be met by the farmers for dairy resale. Change of diet, stress or mastitis lead to higher SCC levels, thus lowering the quality of the milk and consequently lowering the price per unit volume. A cheap cell counter will help farmers and diary producers monitor SCC-levels.

Figure 5:
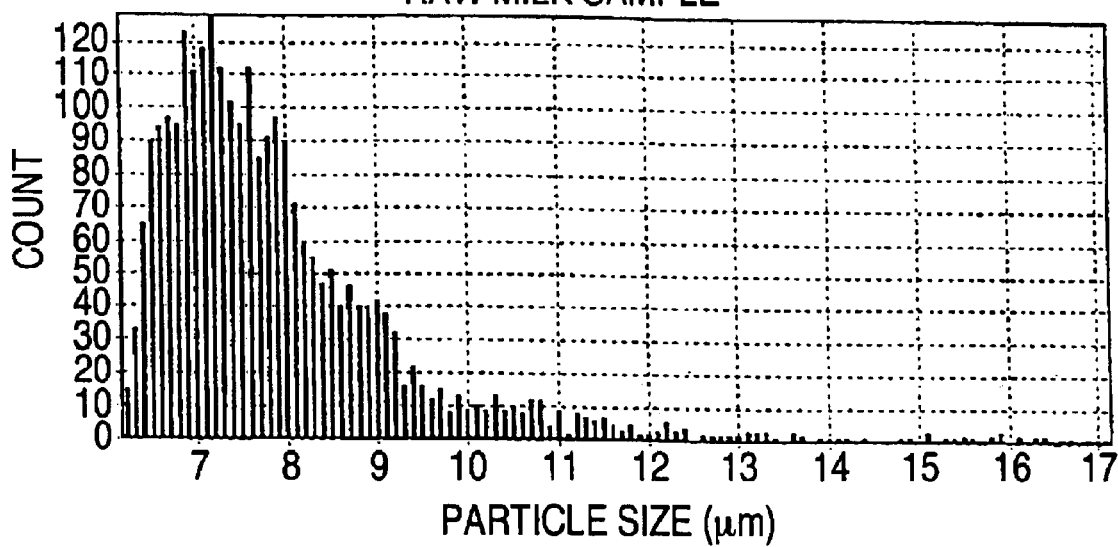
FIG. 5 is a graph showing results obtained in Example 4.

Samples of milk were obtained through the laboratory of the Danish Dairy Board in Ladelund. Milk contains a large number of fat mono-globules of 5–8 µm size, which are evenly distributed in the fresh milk. In order to count the somatic cells the fat has to be removed or distinguished from the somatic cells. In FIG. 5 the results of counting full milk with our Coulter counter set-up are shown. The great majority of small fat cells can clearly be discerned. The SCC can be derived from this count by making a differentiation based on the large differences of sizes of fat particles and somatic cells.

Counting with the standard Fossomatic (Foss, Hilleroed, Denmark) and impedance method is not directly comparable. The Fossomatic measures optical signals from propidium-iodide fluorescent marked particles, which is a marker for DNA. Where the Fossomatic only counts particles with DNA, the impedance method differentiates the Somatic cells from their size. However, a small overlapping of fat particles and Somatic cells are present and must be compensated. By subtraction of 10% of the fat count from the Somatic cell count the impedance counting will detect occurrences of mastitis just as well as the Fossomatic (see FIG. 6).

What is claimed is:

1. Apparatus for characterizing cells in a biological liquid sample, comprising a sensor unit and a docking station for removably receiving the sensor unit,
   the sensor unit adapted for collection and storage of the liquid sample before and after measurement, and comprising:
      a housing with
         a first chamber for holding the biological liquid sample before measurement,
         a collection chamber for collection of the liquid sample after measurement and having an inlet/outlet for connection to a source of positive or negative gas pressure,
         a wall separating the first chamber and the collection chamber and containing an orifice for the passage of the cells from the first chamber to the collection chamber, and
         a first electrode in the first chamber and a second electrode in the collection chamber, each electrode being electrically connected to a respective terminal member accessible from the exterior of the sensor unit,
   the docking station comprising
      a port for connection with the source of positive or negative gas pressure and forming a gas connection with the inlet/outlet when the sensor unit is received in the docking station, and
      electrical connector members for connecting to the respective terminal members when the sensor unit is received in the docking station.

2. Apparatus according to claim 1, wherein the orifice is formed in a polymer.

3. Apparatus according to claim 1, wherein the first chamber has a breather inlet/outlet for communication with atmosphere.

4. Apparatus according to claim 1, wherein the inlet/outlet of the collection chamber of the sensor unit leads from a head space in the collection chamber through a conduit formed in the housing to a port in the housing which co-operates with the port of the docking station.

5. Apparatus according to claim 1, wherein the apparatus includes means for determining the beginning and end of a period during which a predetermined volume of liquid has passed through the orifice.

6. Apparatus according to claim 5, comprising a secondary electrode in one of the first chamber and the collection chamber positioned for sensing when liquid in the chamber is at or above a first level; which secondary electrode is connected to a terminal member accessible from the exterior of the sensor unit, and wherein the docking station comprises an electrical connector member for connecting to the terminal member of the secondary electrode.

7. Apparatus according to claim 6, comprising a further secondary electrode in the same chamber as the secondary electrode and positioned for sensing when liquid in the chamber is at or above a second level, which further secondary electrode is connected to another terminal member accessible from the exterior of the sensor unit, and wherein the docking station comprises another electrical connector member for connecting to the another terminal member of the further secondary electrode.

8. Apparatus according to claim 1, wherein each of the first chamber and the collection chamber has a transverse cross-sectional area at a level of the orifice which is substantially less than a transverse cross-sectional area of the respective chamber over a substantial part of a height of the chamber above the orifice.

9. A sensor unit for characterizing cells suspended in a biological liquid sample and adapted to be removably received in a docking station, comprising a housing adapted for collection and storage of the liquid sample before and after measurement, and including
    a first chamber for holding the biological liquid sample before measurement,
    a collection chamber for collection of the liquid sample after measurement and having an inlet/outlet for connection to a source of positive or negative gas pressure,
    a wall separating the first chamber and the collection chamber and containing an orifice for the passage of the cells from the first chamber to the collection chamber, and
    a first electrode in the first chamber and a second electrode in the collection chamber, each electrode being electrically connected to a respective terminal member accessible from the exterior of the sensor unit, in such a way that, when the sensor unit is received in the docking station, the inlet/outlet is operationally connected with a port in the docking station for connection with the source of positive or negative gas pressure and electrical connector members are operationally connected to the respective terminal members.

10. Sensor unit according to claim 9, wherein the orifice is formed in a polymer.

11. Sensor unit according to claim 9, wherein the first chamber has a breather inlet/outlet for communication with atmosphere.

12. Sensor unit according to claim 9, wherein the inlet/outlet of the collection chamber of the sensor unit leads from a head space in the collection chamber through a conduit formed in the housing to a port in the housing which co-operates with the port of the docking station.

13. Sensor unit according to claim 9, wherein the sensor unit includes means for determining the beginning and end of a period during which a predetermined volume of liquid has passed through the orifice.

14. Sensor unit according to claim 13, comprising a secondary electrode in one of the first chamber and the collection chamber positioned for sensing when liquid in the chamber is at or above a first level, which secondary electrode is connected to a terminal member accessible from the exterior of the sensor unit.

15. Sensor unit according to claim 14, comprising a further secondary electrode in the same chamber as the secondary electrode and positioned for sensing when liquid in the chamber is at or above a second level, which further secondary electrode is connected to another terminal member accessible from the exterior of the sensor unit.

16. Sensor unit according to claim 9, wherein each of the first chamber and the collection chamber has a transverse cross-sectional area at a level of the orifice which is substantially less than a transverse cross-sectional area of the respective chamber over a substantial part of a height of the chamber above the orifice.

17. A method of operating a particle characterization apparatus comprising:

a sensor unit that is demountable from the apparatus and contains a first chamber for holding a biological liquid sample, and a collection chamber separated by a wall containing an orifice for passage of cells from the first chamber to the collection chamber that initially contains a volume of air and has a connection to an air pump for pumping liquid through the orifice into the collection chamber, and further comprising a first electrode in the first chamber and a second electrode in the collection chamber, each electrode being electrically connected to a respective terminal member accessible from the exterior of the sensor unit, the apparatus further comprising electrical connector members that are operationally connected to the respective terminal members when the sensor unit is received in the docking station, the method comprising passing a biological liquid sample containing cells from the first chamber, through the orifice, and into the collection chamber, making cell characterizing measurements for a period in such a way that the liquid does not flow out of the collection chamber, disconnecting the sensor unit from the apparatus with all of the liquid sample that has passed into the collection chamber, and discarding the sensor unit.

* * * * *